(12) United States Patent
Papas

(10) Patent No.: US 11,723,558 B2
(45) Date of Patent: Aug. 15, 2023

(54) ENCAPSULATION DEVICE SYSTEMS WITH OXYGEN SENSORS WITH OR WITHOUT EXOGENOUS OXYGEN DELIVERY

(71) Applicant: ARIZONA BOARD OF REGENTS ON BEHALF OF THE UNIVERSITY OF ARIZONA, Tucson, AZ (US)

(72) Inventor: Klearchos K. Papas, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 1090 days.

(21) Appl. No.: 16/347,338

(22) PCT Filed: Nov. 3, 2017

(86) PCT No.: PCT/US2017/060036
§ 371 (c)(1),
(2) Date: May 3, 2019

(87) PCT Pub. No.: WO2018/085714
PCT Pub. Date: May 11, 2018

(65) Prior Publication Data
US 2019/0328289 A1 Oct. 31, 2019

Related U.S. Application Data

(60) Provisional application No. 62/417,005, filed on Nov. 3, 2016.

(51) Int. Cl.
*A61B 5/145* (2006.01)
*A61B 5/00* (2006.01)
*A61F 2/02* (2006.01)

(52) U.S. Cl.
CPC ...... *A61B 5/14503* (2013.01); *A61B 5/14532* (2013.01); *A61B 5/14539* (2013.01);
(Continued)

(58) Field of Classification Search
CPC .... A61F 2/022; A61F 2/0095; A61B 5/14503; A61B 5/0031; A61B 5/14542;
(Continued)

(56) References Cited

U.S. PATENT DOCUMENTS

| 4,902,476 A | 2/1990 | Gordon et al. |
| 5,169,390 A | 12/1992 | Athayde et al. |

(Continued)

FOREIGN PATENT DOCUMENTS

| CA | 3042709 | 8/2018 |
| CN | 101123984 | 2/2008 |

(Continued)

OTHER PUBLICATIONS

Official Action for Australian Patent Application No. 2017355528, dated Aug. 20, 2020, 5 pages.

(Continued)

*Primary Examiner* — Eric J Messersmith
(74) *Attorney, Agent, or Firm* — Sheridan Ross P.C.

(57) ABSTRACT

An encapsulation device system for therapeutic applications such as but not limited to regulating blood glucose. The system may comprise an encapsulation device with a first oxygen sensor integrated inside the device and a second oxygen sensor disposed on an outer surface of the device, wherein the sensors allow for real-time measurements (such as oxygen levels) related to cells (e.g., islet cells, stem cell derived beta cells, etc.) housed in the encapsulation device. The system may also feature an exogenous oxygen delivery system operatively connected to the encapsulation device via a channel, wherein the exogenous oxygen delivery system is adapted to deliver oxygen to the encapsulation device.

17 Claims, 2 Drawing Sheets

(52) U.S. Cl.
CPC ...... *A61B 5/14542* (2013.01); *A61B 5/14546* (2013.01); *A61B 5/4836* (2013.01); *A61B 5/686* (2013.01); *A61F 2/022* (2013.01)

(58) Field of Classification Search
CPC ............ A61B 5/14546; A61B 5/14532; A61B 5/4836; A61B 5/14551; A61B 5/686; A61B 5/14539; A61M 5/14
See application file for complete search history.

(56) References Cited

U.S. PATENT DOCUMENTS

| | | | |
|---|---|---|---|
| 5,324,518 A | 6/1994 | Orth et al. | |
| 5,368,028 A | 11/1994 | Palti | |
| 5,595,621 A | 1/1997 | Light et al. | |
| 5,626,561 A | 5/1997 | Butler et al. | |
| 5,713,888 A | 2/1998 | Neuenfeldt et al. | |
| 5,741,330 A * | 4/1998 | Brauker | A61L 27/56 623/920 |
| 5,814,405 A | 9/1998 | Branca et al. | |
| 5,837,234 A | 11/1998 | Yapel et al. | |
| 5,843,069 A | 12/1998 | Butler et al. | |
| 5,980,889 A | 11/1999 | Butler et al. | |
| 6,060,640 A | 5/2000 | Pauley et al. | |
| 6,143,293 A | 11/2000 | Weiss et al. | |
| 6,156,305 A | 12/2000 | Brauker et al. | |
| 6,197,575 B1 | 3/2001 | Griffith et al. | |
| 6,562,616 B1 | 5/2003 | Toner et al. | |
| 7,659,219 B2 | 2/2010 | Biran et al. | |
| 7,899,927 B1 | 2/2011 | Vardi et al. | |
| 8,278,106 B2 | 10/2012 | Martinson et al. | |
| 8,518,123 B2 | 8/2013 | Jensen et al. | |
| 8,647,861 B2 | 2/2014 | Ingber et al. | |
| 9,433,557 B2 | 9/2016 | Green et al. | |
| 10,695,379 B2 | 6/2020 | Greenwood et al. | |
| 11,033,666 B2 | 6/2021 | Ferrante et al. | |
| 2003/0054544 A1 | 3/2003 | Gruenberg | |
| 2003/0087427 A1 | 5/2003 | Colton et al. | |
| 2003/0129736 A1 | 7/2003 | Mitrani | |
| 2004/0010320 A1 | 1/2004 | Huckle et al. | |
| 2004/0024342 A1 | 2/2004 | Weitzel et al. | |
| 2004/0133188 A1 | 7/2004 | Vardi et al. | |
| 2004/0166141 A1 | 8/2004 | Cerami et al. | |
| 2004/0197374 A1 | 10/2004 | Rezania et al. | |
| 2005/0136092 A1 | 6/2005 | Rotem et al. | |
| 2005/0221485 A1 | 10/2005 | Bader | |
| 2005/0267440 A1 | 12/2005 | Herman et al. | |
| 2006/0013835 A1 | 1/2006 | Anderson et al. | |
| 2006/0019333 A1 | 1/2006 | Rodgers et al. | |
| 2007/0061015 A1 | 3/2007 | Jensen et al. | |
| 2007/0066138 A1 | 3/2007 | Ferrari et al. | |
| 2008/0021436 A1* | 1/2008 | Wolpert | H01L 23/49548 600/365 |
| 2009/0074832 A1 | 3/2009 | Zussman et al. | |
| 2009/0110669 A1 | 4/2009 | Schneiderman et al. | |
| 2010/0082114 A1 | 4/2010 | Gingras et al. | |
| 2010/0124564 A1 | 5/2010 | Martinson et al. | |
| 2010/0130916 A1 | 5/2010 | Stern et al. | |
| 2010/0160760 A1 | 6/2010 | Shults et al. | |
| 2010/0172952 A1 | 7/2010 | Srouji et al. | |
| 2010/0196439 A1 | 8/2010 | Beck et al. | |
| 2010/0228110 A1 | 9/2010 | Tsoukalis | |
| 2010/0240117 A1 | 9/2010 | Ying et al. | |
| 2010/0255059 A1 | 10/2010 | Marquez et al. | |
| 2011/0054589 A1 | 3/2011 | Bashiri et al. | |
| 2011/0092949 A1 | 4/2011 | Wang | |
| 2012/0245705 A1 | 9/2012 | Hasilo et al. | |
| 2013/0289540 A1 | 10/2013 | Zeltser et al. | |
| 2013/0344131 A1 | 12/2013 | Lo et al. | |
| 2014/0014226 A1 | 1/2014 | Green et al. | |
| 2014/0039383 A1 | 2/2014 | Dobbles et al. | |
| 2014/0051162 A1 | 2/2014 | Nankervis | |
| 2014/0052095 A1 | 2/2014 | Dobbles et al. | |
| 2014/0088347 A1 | 3/2014 | Frigstad et al. | |
| 2014/0257515 A1 | 9/2014 | So et al. | |
| 2014/0308315 A1 | 10/2014 | Knezevich et al. | |
| 2015/0129497 A1 | 5/2015 | Humes et al. | |
| 2015/0112247 A1 | 8/2015 | Tempelman et al. | |
| 2015/0273200 A1* | 10/2015 | Rotem | A61M 5/14276 604/23 |
| 2015/0320836 A1 | 11/2015 | Itkin-Ansari et al. | |
| 2015/0359672 A1 | 12/2015 | Botvinick et al. | |
| 2016/0022180 A1 | 1/2016 | Joseph et al. | |
| 2016/0123848 A1 | 5/2016 | Griffin et al. | |
| 2016/0184569 A1* | 6/2016 | Lathuiliere | A61P 1/18 604/93.01 |
| 2017/0072074 A1 | 3/2017 | Gladnikoff et al. | |
| 2017/0173262 A1 | 6/2017 | Veltz | |
| 2018/0000395 A1* | 1/2018 | Lucisano | A61B 5/14532 |
| 2018/0126134 A1 | 5/2018 | Cully et al. | |
| 2018/0263238 A1 | 9/2018 | Flanagan et al. | |
| 2018/0298343 A1 | 10/2018 | Sivakumaran | |
| 2018/0318566 A1 | 11/2018 | Ferrante et al. | |
| 2018/0344665 A1 | 12/2018 | Isenburg et al. | |
| 2019/0076840 A1* | 3/2019 | Gottardi | C12M 41/36 |
| 2019/0136176 A1 | 5/2019 | Kawachi et al. | |
| 2019/0211294 A1 | 7/2019 | Karnieli | |
| 2019/0336267 A1 | 11/2019 | Tempelman et al. | |
| 2020/0054257 A1 | 2/2020 | Papas | |
| 2020/0063085 A1 | 2/2020 | Papas | |

FOREIGN PATENT DOCUMENTS

| | | |
|---|---|---|
| CN | 102012390 | 4/2011 |
| CN | 203915611 | 11/2014 |
| CN | 105163688 | 12/2015 |
| CN | 105792775 | 7/2016 |
| EP | 0344314 A1 * | 12/1989 |
| EP | 1351623 B1 | 1/2005 |
| EP | 2508212 | 10/2012 |
| JP | H06-205665 | 7/1994 |
| JP | 2004-530431 | 10/2004 |
| JP | 2014-514942 | 6/2014 |
| KR | 10-2016-0094391 | 8/2016 |
| WO | WO 91/00119 | 1/1991 |
| WO | WO 02/100335 | 12/2002 |
| WO | WO 2006/106506 | 10/2006 |
| WO | WO 2008/100559 | 8/2008 |
| WO | WO2010061387 A2 | 6/2010 |
| WO | WO 2012/136701 | 10/2012 |
| WO | WO2015145264 A2 | 10/2015 |
| WO | WO2018067813 A1 | 4/2018 |
| WO | WO 2018/089397 | 5/2018 |
| WO | WO2018085714 A1 | 5/2018 |
| WO | WO2018102077 A1 | 6/2018 |
| WO | WO2018144098 A1 | 8/2018 |
| WO | WO2018144099 A1 | 8/2018 |

OTHER PUBLICATIONS

Official Action for Australian Patent Application No. 2017396753, dated Jul. 23, 2020, 4 pages.

Lathuiliere et al. "Encapsulated Cellular Implants for Recombinant Protein Delivery and Therapeutic Modulation of the Immune System." International Journal of Molecular Sciences. May 2015 (May 8, 2015). vol. 16. pp. 10578-10600.

Lee et al. Cytokines in Cancer Immunotherapy. Cancers 2011, 3, 3856-3893.

Manickavasagam et al. Critical Assessment of Implantable Drug Delivery Devices in Glaucoma Management. Journal of Drug Delivery. vol. 2013, Article ID 895013, pp. 1-12.

Makadia et al. Poly Lactic-co-Glycolic Acid (PLGA) as Biodegradable Controlled Drug Delivery Carrier. Polymers (Basel). Sep. 1, 2011; 3(3): 1377-1397.

Gholipourmalekabadi et al. Oxygen-Generating Biomaterials: A New, Viable Paradigm for Tissue Engineering? Trends in Biotechnology, Dec. 2016, vol. 34, No. 12.

Geller et al. Use of an Immunoisolation Device for Cell Transplantation and Tumor Immunotherapy. Annals New York Academy of Sciences. pp. 438-451.

International Search Report for PCT Application No. PCT/US17/55334 dated Dec. 26, 2017.

(56) References Cited

OTHER PUBLICATIONS

Carlsson et al. Transplantation of macroencapsulated human islets within the bioartificial pancreas βAir to patients with type 1 diabetes mellitus. Am J Transplant. 2018;18:1735-1744.
ViaCyte CEO Paul Laikind Interview: Trial Update, Melton's Concerns, & Future. https://ipscell.com/2015/03/viacyte/.
International Search Report for PCT Application No. PCT/US17/60036 dated Feb. 16, 2018.
International Search Report for PCT Application No. PCT/US17/60034 dated Jul. 12, 2018.
International Search Report for PCT Application No. PCT/US17/60041 dated Jul. 10, 2018.
International Search Report for PCT Application No. PCT/US17/60043 dated Jun. 14, 2018.
"Membrane Basics," PermSelect—Silicone Gas Exchange Membranes, 2021, retrieved from https://www.permselect.com/membranes, 9 pages.
Notice of Acceptance for Australia Patent Application No. 2017396753, dated Apr. 20, 2021, 4 pages.
Official Action (with English translation) for China Patent Application No. 201780081104.1, dated Apr. 2, 2021, 10 pages.
Official Action for U.S. Appl. No. 16/347,388, dated May 11, 2021, 10 pages.
Official Action for U.S. Appl. No. 16/347,147, dated Jul. 2, 2021, 12 pages.
U.S. Appl. No. 16/347,388, filed May 3, 2019, Papas.
Extended European Search Report for European Patent Application No. 17866485.0, dated Apr. 25, 2020, 9 pages.
Extended European Search Report for European Patent Application No. 17895433.5, dated Apr. 17, 2020, 7 pages.
Extended European Search Report for European Patent Application No. 17894862.6, dated May 20, 2020, 4 pages.
Official Action for Australian Patent Application No. 2017366791, dated Jun. 22, 2020, 4 pages.
Extended European Search Report for European Patent Application No. 17875181.4, dated Apr. 28, 2020, 4 pages.
Krishnan et al., "Islet and Stem Cell Encapsulation for Clinical Transplantation," Review of Diabetic Studies, vol. 11, No. 1, 2014, pp. 84-101.
Wang et al., "Overcoming foreign-body reaction through nanotopography: Biocompatibility and Immunoisolation properties of a nanofibrous membrane," Biomaterials, vol. 102, Sep. 30, 2016, pp. 249-258.
Official Action for Australian Patent Application No. 2017355528, dated Nov. 16, 2020, 4 pages.
Notice of Acceptance for Australian Patent Application No. 2017355528, dated Mar. 22, 2021, 4 pages.
Official Action for Chinese Patent Application No. 201780081318.9, dated Feb. 1, 2021, 8 pages.
Official Action for Australian Patent Application No. 2017396753, dated Jan. 27, 2021, 5 pages.
Official Action for Australian Patent Application No. 2017396754, dated Nov. 12, 2020, 7 pages.
Official Action for Chinese Patent Application No. 201780081103.7, dated Jan. 11, 2021, 11 pages.
Notice of Allowance for Australian Patent Application No. 2017366791, dated Jan. 8, 2021, 4 pages.
International Search Report and Written Opinion for International (PCT) Patent Application No. PCT/US2019/052728, dated Dec. 13, 2019, 10 pages.
Official Action for U.S. Appl. No. 16/347,147, dated Apr. 8, 2021, 8 pages. Restriction Requirement.
Official Action for U.S. Appl. No. 16/347,160, dated Dec. 28, 2020, 15 pages.
Official Action for Korea Patent Application No. 10-2019-7015936, dated Jul. 25, 2022, 5 pages.
Official Action for China Patent Application No. 201780081104.1, dated Jun. 30, 2022, 27 pages.
Notice of Allowance for Korea Patent Application No. 10-2019-7015935, dated Jul. 25, 2022, 3 pages.
Notice of Allowance for Korea Patent Application No. 10-2019-7015937, dated Jul. 22, 2022, 3 pages.
Official Action for China Patent Application No. 201780081105.6, dated Sep. 29, 2022, 8 pages.
Official Action for Australia Patent Application No. 2019346547, dated Sep. 2, 2022, 4 pages.
Extended European Search Report for Europe Patent Application No. 19867716.3, dated Oct. 6, 2022, 12 pages.
Official Action (with English summary) for Japan Patent Application No. 2021-540389, dated Jun. 21, 2022, 7 pages.
Official Action for U.S. Appl. No. 16/347,160, dated Jul. 7, 2022, 14 pages.
Official Action for U.S. Appl. No. 17/876,302, dated Oct. 25, 2022, 22 pages.
Official Action for Australia Patent Application No. 2021204321, dated Jun. 6, 2022, 3 pages.
Official Action for China Patent Application No. 201780081318.9, dated Sep. 1, 2021, 12 pages.
Official Action for China Patent Application No. 201780081318.9, dated Apr. 7, 2022, 22 pages.
Official Action for Korea Patent Application No. 10-2019-7015936, dated Feb. 22, 2022, 11 pages.
Official Action for Australia Patent Application No. 202106840, dated Jun. 6, 2022, 3 pages.
Official Action for China Patent Application No. 201780081104.1, dated Dec. 2, 2021, 11 pages.
Official Action for Korea Patent Application No. 10-2019-7015935, dated Feb. 8, 2022, 9 pages.
Notice of Allowance for Australian Patent Application No. 2017396754, dated Jul. 21, 2021, 4 pages.
Official Action for China Patent Application No. 201780081103.7, dated Nov. 1, 2021, 11 pages.
Notice of Allowance for China Patent Application No. 201780081103.7, dated Mar. 23, 2022, 2 pages.
Official Action for Korea Patent Application No. 10-2019-7015937, dated Jan. 12, 2022, 14 pages.
Notice of Allowance for Korea Patent Application No. 10-2019-7015937, dated May 20, 2022, 6 pages.
Official Action for China Patent Application No. 201780081105.6, dated Aug. 9, 2021, 12 pages.
Official Action for China Patent Application No. 201780081105.6, dated Mar. 24, 2022, 12 pages.
Official Action for Korea Patent Application No. 10-2019-7015938, dated Sep. 30, 2021, 5 pages.
International Preliminary Report on Patentability for International (PCT) Application No. PCT/US2019/052728, dated Apr. 1, 2021, 9 pages.
Official Action for Australia Patent Application No. 2019346547, dated Feb. 9, 2022, 4 pages.
Official Action for Canada patent Application No. 3114197, dated Jun. 6, 2022, 6 pages.
Partial Supplementary European Search Report for Europe Patent Application No. 19867716.3, dated May 23, 2022, 13 pages.
Official Action for India Patent Application No. 202117012735, dated Feb. 11, 2022, 5 pages.
Invitation to Pay additional Fees for International (PCT) Patent Application No. PCT/US2021/057526, dated Jan. 5, 2022, 3 pages.
International Search Report and Written Opinion for International (PCT) Patent Application No. PCT/US2021/057526, dated Mar. 2, 2022, 16 pages.
Official Action for U.S. Appl. No. 16/347,388, dated Oct. 4, 2021, 10 pages.
Notice of Allowance for U.S. Appl. No. 16/347,388, dated May 12, 2022, 10 pages.
Corrected Notice of Allowance for U.S. Appl. No. 16/347,388, dated May 20, 2022, 6 pages.
Official Action for U.S. Appl. No. 16/347,147, dated Nov. 12, 2021, 11 pages.
Official Action for U.S. Appl. No. 16/347,147, dated Jun. 2, 2022, 14 pages.
Official Action for U.S. Appl. No. 16/347,160, dated Nov. 29, 2021, 14 pages.

(56) References Cited

OTHER PUBLICATIONS

Official Action for U.S. Appl. No. 17/387,595, dated Nov. 10, 2021, 15 pages.
Official Action for U.S. Appl. No. 17/387,595, dated Mar. 28, 2022, 18 pages.
Suszynski et al., "Assessment of Tissue-Engineered Islet Graft Viability by Fluorine Magnetic Resonance Spectroscopy," Transplant Proc., vol. 43, No. 9, Nov. 2011, pp. 3221-3225.

* cited by examiner

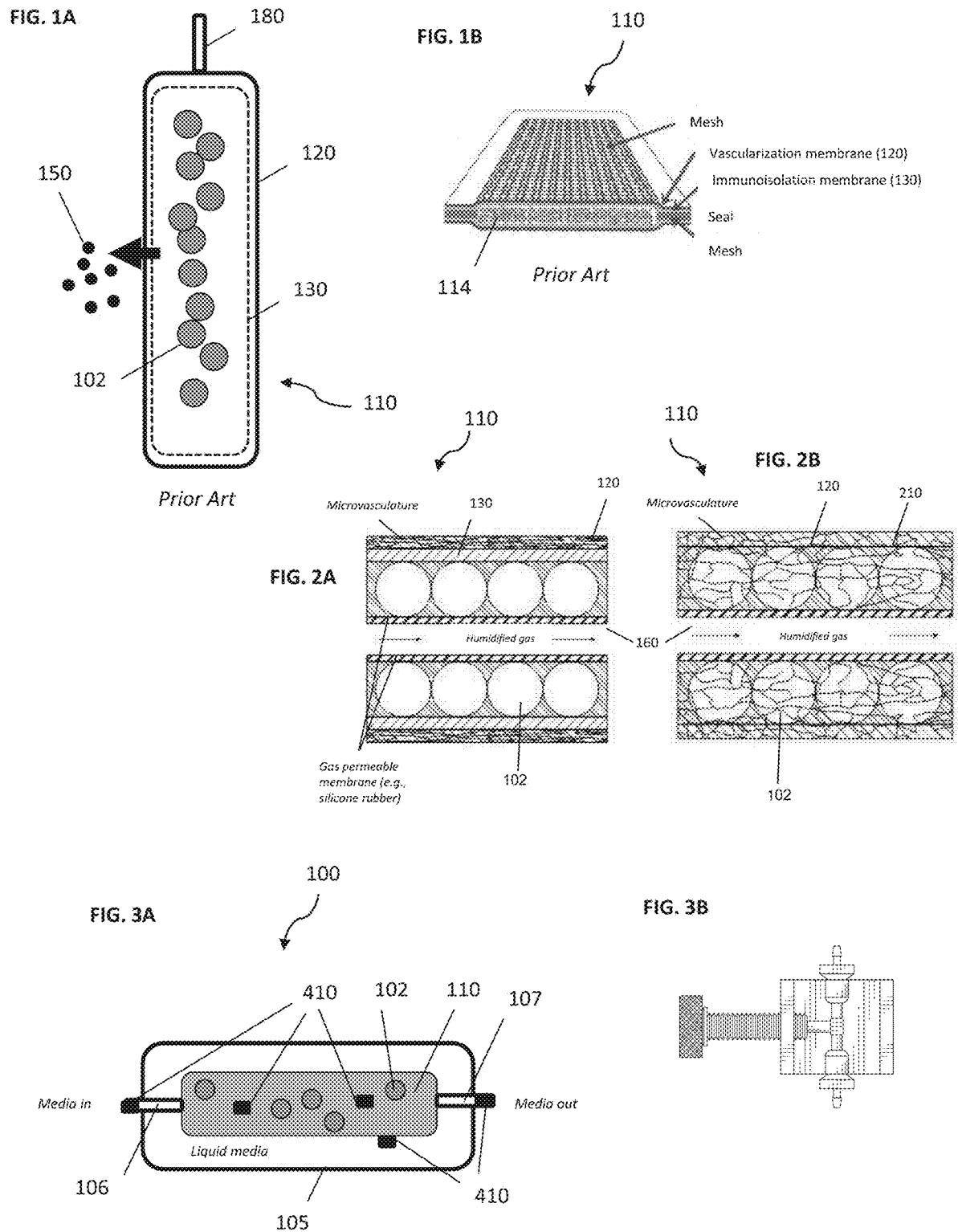

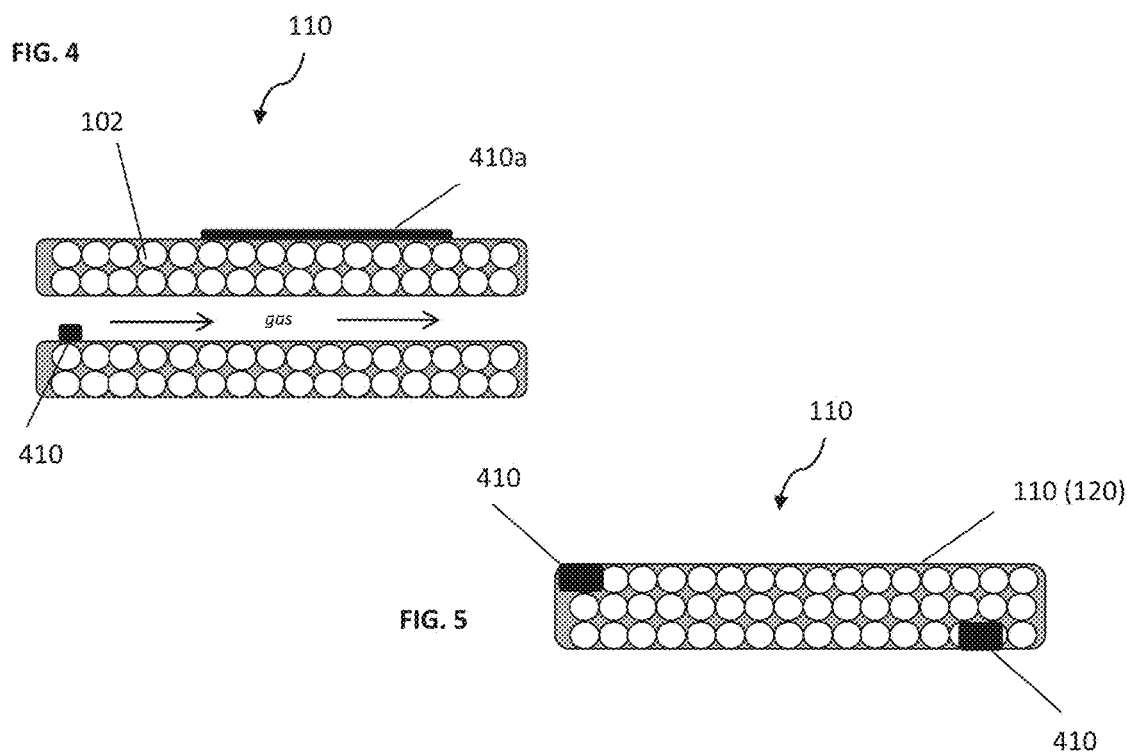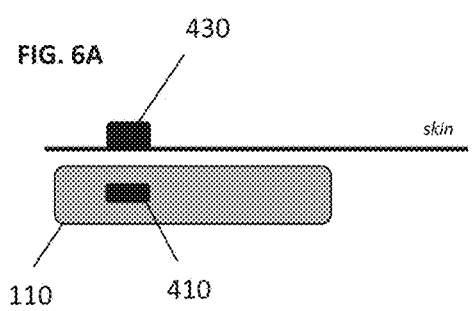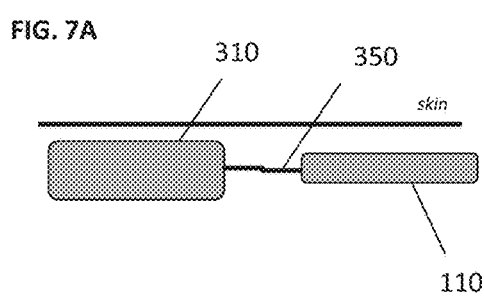

ENCAPSULATION DEVICE SYSTEMS WITH OXYGEN SENSORS WITH OR WITHOUT EXOGENOUS OXYGEN DELIVERY

CROSS REFERENCE

This application is a 371 and claims benefit of PCT/US17/60036 filed Nov. 3, 2017, which claims benefit of U.S. Patent Application No. 62/417,005, filed Nov. 3, 2016, the specification(s) of which is/are incorporated herein in their entirety by reference.

GOVERNMENT SUPPORT

This invention was made with government support under Grant No. DK106933, awarded by NIH. The government has certain rights in the invention.

FIELD OF THE INVENTION

The present invention relates to encapsulation devices for cells (such as but not limited to islet cells, stem cell derived beta cells, or the like, e.g., for regulating blood glucose, or other cells or spheroids that can produce and release a therapeutic agent that is useful in the body), more particularly to encapsulation devices with oxygen sensors and an exogenous oxygen or gas delivery system creating a closed-loop system.

BACKGROUND OF THE INVENTION

The present invention features systems with encapsulation devices for cells (such as islet cells or stem cell derived beta cells or the like) and sensors for real-time monitoring of cells or analytes (such as oxygen levels, glucose levels, pH, lactate levels, carbon dioxide levels, etc.). The encapsulation devices may be loaded with cells or may be empty. The systems may be operatively connected to an oxygen generator or a gas delivery system (e.g., an air pump, a chemical oxygen generator, etc.). The sensors may be optical, electrochemical, or a combination thereof.

In some embodiments, the system (e.g., encapsulation device with oxygen sensors) and oxygen generator (or gas delivery system) are in a closed loop with the sensor reader that can regulate the delivery of oxygen or other gas to the device based on the levels of oxygen that the sensor is reading from the sensors. The integration of sensors into the device (e.g., a sensor inside the device, a sensor on the outside of the device, two sensors inside the device, etc.) can help provide measurements (e.g., oxygen, glucose, lactate, pH, carbon dioxide, etc.) at various stages including, but not limited to, pre-implantation and post-implantation.

In some embodiments, the systems (e.g., encapsulation devices with sensors, e.g., oxygen sensors) of the present invention are used with oxygen delivery. In some embodiments, the systems (e.g., encapsulation devices with oxygen sensors) of the present invention are used without oxygen delivery. In some embodiments, the systems (e.g., encapsulation devices with oxygen sensors) of the present invention are temporarily oxygenated.

As used herein, the term "oxygen delivery" also includes gas delivery, e.g., air delivery. The term "oxygen generator" also refers to a gas generator.

Without wishing to limit the present invention to any theory or mechanism, it is believed that the methods, systems (e.g., encapsulation devices with oxygen sensors), devices, and compositions of the present invention may help detect and regulate oxygen levels near or within encapsulation devices and alarm if not within the desired level. If insulin secreting cells are transplanted, the system may help regulate blood glucose by ensuring that the insulin secreting cells are properly oxygenated and therefore are able to release insulin in response to glucose in an appropriate manner.

The disclosures of the following U.S. Patents are incorporated in their entirety by reference herein: U.S. Pat. No. 5,713,888; U.S. Pat. App. No. 2003/0087427.

SUMMARY OF THE INVENTION

The present invention features systems with encapsulation devices for cells (such as islet cells or stem cell derived beta cells or the like) and sensors for real-time monitoring of cells or analytes or various features of the encapsulation device like oxygen levels, pH, lactate levels, etc. The systems may be operatively connected to oxygen generators or gas/oxygen delivery systems. In some embodiments, the system (e.g., encapsulation device with oxygen sensors) and oxygen generator are in a closed loop with the sensor reader that can regulate the delivery of oxygen to the device based on the levels of oxygen that the sensor is reading from the sensors. The integration of sensors into the device (e.g., a sensor inside the device, a sensor on the outside of the device, two sensors inside the device, etc.) can help provide measurements (e.g., oxygen, glucose, lactate, pH, carbon dioxide, etc.) at various stages including, but not limited to, pre-implantation and post-implantation.

The present invention features a system comprising: an encapsulation device comprising a lumen for holding cells surrounded by a vascularization membrane; and a sensor (or two or more sensors, e.g., two sensors, three sensors, four sensors, etc.) for monitoring (e.g., real-time monitoring) of a feature of the cells housed in the encapsulation device. The feature may be oxygen levels, oxygen consumption, glucose levels, lactate levels, pH, insulin levels, the like, or a combination thereof.

In some embodiments, the sensor(s) are disposed on an outer surface of the encapsulation device, within the encapsulation device, or on other locations (e.g., inlets, outlets, etc.), or a combination thereof. For example, in some embodiments, the system comprises a sensor disposed on the outlet of the encapsulation device and a sensor disposed on the inlet of an encapsulation device.

In some embodiments, the system further comprises a bioreactor for housing the encapsulation device.

In some embodiments, the sensor comprises a pair of oxygen sensors for measuring oxygen consumption rate of the cells housed in the encapsulation device.

In some embodiments, the system further comprises an oxygen delivery system or gas delivery system operatively connected to the encapsulation device. The oxygen delivery system may comprise an implantable oxygen generator. The oxygen delivery system may comprise a wearable oxygen generator. In some embodiments, the oxygen delivery system (or gas delivery system) delivers oxygen or gas to the encapsulation device temporarily. In some embodiments, the oxygen delivery system (or gas delivery system) delivers oxygen or gas to the encapsulation device as needed. In some embodiments, the sensor is an oxygen sensor, glucose sensor, pH sensor, lactate sensor, $CO_2$ sensor, or a combination thereof. In some embodiments, the sensors are placed such that they do not interfere with each other.

In some embodiments, the encapsulation device comprises two lumens separated by a gas channel. In some embodiments, the oxygen delivery system (or gas delivery system) is fluidly connected to the gas channel. In some embodiments, the sensor is disposed in the gas channel.

In some embodiments, the system further comprises a reader adapted to read the sensor. In some embodiments, the reader is an implantable optical reader.

The present invention also features a system comprising: an encapsulation device comprising a lumen for holding cells surrounded by a vascularization membrane; and a first oxygen sensor disposed on an outlet of the encapsulation device and a second oxygen sensor disposed on an inlet of the encapsulation device; and an oxygen delivery system operatively connected to the encapsulation device via a tube, wherein the oxygen delivery system delivers oxygen to the encapsulation device.

In some embodiments, the oxygen delivery system or gas delivery system comprises an implantable oxygen generator. In some embodiments, the oxygen delivery system comprises a wearable oxygen generator. In some embodiments, the oxygen delivery system delivers oxygen to the encapsulation device temporarily. In some embodiments, the oxygen delivery system delivers oxygen to the encapsulation device as needed. In some embodiments, the encapsulation device comprises two lumens separated by a gas channel. In some embodiments, the oxygen delivery system is fluidly connected to the gas channel. In some embodiments, the system further comprises a sensor reader for reading the sensor. In some embodiments, the sensor reader is an implantable optical reader. In some embodiments, the sensors are operatively connected to the exogenous oxygen delivery system via the sensor reader. In some embodiments, the sensor reader is physically connected to the sensor. In some embodiments, the sensor reader is not physically connected to the sensor.

In some embodiments, upon receipt of a first command from the sensor reader when the sensor reader detects an oxygen level below a threshold level, the exogenous oxygen delivery system activates and delivers oxygen to the encapsulation device. In some embodiments, the system is operatively connected to an alarm system such that an alarm is activated when the sensor reader detects an oxygen level below a threshold level. In some embodiments, upon receipt of a first command from the sensor reader when the sensor reader detects an oxygen level above a threshold level, the exogenous oxygen delivery system deactivates and ceases delivery of oxygen/gas to the encapsulation device. In some embodiments, the system is operatively connected to an alarm system such that an alarm is activated when the sensor reader detects an oxygen level above a threshold level.

In some embodiments, the sensor reader is implantable. In some embodiments, the cells housed in the encapsulation device are islet cells or stem cell derived beta cells. In some embodiments, the system helps regulate blood glucose. In some embodiments, the sensor is an optical sensor. In some embodiments, the system further comprises a detection system for detecting the optical sensor, the detection system comprising an optical reader, wherein the optical reader is constructed from a material that allows implantation of the optical reader in a subject. In some embodiments, the optical reader is implanted adjacent to a sensor. In some embodiments, the optical reader can be implanted into the subject at any depth with respect to the skin.

In some embodiments, the reader is an implantable circuit for electrochemical sensors that send signals outside the body wirelessly.

The present invention also features a method of detecting vascularization of an encapsulation device (e.g., a cell free device) according to the present invention (e.g., comprising a lumen for holding cells surrounded by a vascularization membrane and a first oxygen sensor disposed on an outlet of the encapsulation device and a second oxygen sensor disposed on an inlet of the encapsulation device). In some embodiments, the method comprises detecting oxygen levels via the sensors, wherein an increase in oxygen level above zero (or above a certain threshold level) is indicative of vascularization of the encapsulation device. In some embodiments, the encapsulation device is absent of cells.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which:

FIG. 1A shows an example of a single-chamber encapsulation device for holding cells or tissues. The device comprises a port to access the lumen for loading the cells or tissue.

FIG. 1B shows a cross-sectional view of the device of FIG. 1A. The cells are encapsulated in a two-layer membrane envelope formed using a mesh insert. The device comprises a vascularization membrane and an immunoisolation membrane. The present invention is not limited to devices that utilize an immunoisolation membrane: in some embodiments, the device only comprises the vascularization membrane.

FIG. 2A shows a detailed view of an encapsulation device with an immunoisolation membrane.

FIG. 2B shows a detailed view of an encapsulation device without the immunoisolation membrane.

FIG. 3A shows a schematic view of a system comprising a bioreactor containing and encapsulation device with cells. Sensors are disposed within the encapsulation devices as well as on the surface of the device. Sensors are also disposed on the inlet and outlet of the system (bioreactor), e.g., in combination with a flow through cell. In some embodiments, the sensors on the inlet and outlet of the system are for oxygen consumption rate measurements (which may be used as a means of evaluating viability of the device with cells). The media (from a first media reservoir) enters through the inlet of the encapsulation device and exits through the outlet to a second media reservoir.

FIG. 3B shows an example of a flow through cell for liquid or gas entering a bioreactor with an opening for sensor and/or optical reader (e.g., metal screw). This may be connected to tubing (e.g., hose barb fittings) with fluid going in and out while a sensor can measure the oxygen or other analyte concentration.

FIG. 4 shows a schematic view of a system comprising an encapsulation device with two lumens of cells separated by a gas channel. A sensor is disposed in the gas channel, and sensing particles are disposed on the outer surface of the device. Sensors may be at various different locations.

FIG. 5 shows a schematic view of an encapsulation device (single-chamber) comprising two sensors disposed in the lumen with the cells. As previously discussed, the sensors may be various types of sensors, e.g., oxygen sensor, glucose sensor, lactate sensor, combination thereof, etc.

FIG. 6A shows a schematic view of a system with an optical reader outside the body. The wireless reader is external to the skin. The wireless reader can read the sensors in the device below the skin.

FIG. 6B shows a schematic view of a system with an optical reader inside the body. The reader can read the sensors in the device, even through vasculature.

FIG. 7A shows a schematic view of a system (encapsulation device) operatively connected to an implantable oxygen generator.

FIG. 7B shows a schematic view of a system (encapsulation device) operatively connected to a wearable oxygen generator.

DETAILED DESCRIPTION OF THE INVENTION

Encapsulation Devices

Encapsulation devices are devices for holding cells or tissues. The encapsulation device (110) shown in FIG. 1A is a single-chamber encapsulation device. The device (100) comprises an inner lumen for holding the cells (102) or tissue and at least one membrane, e.g., a vascularization membrane (120), which is impermeable to cells. In some embodiments, the device (100) further comprises an immunoisolation membrane (130). Non-cell factors or molecules (150) can escape the cell impermeable membrane. The device (110) also comprises a port (180) to access the lumen for loading the cells or tissue. FIG. 1B shows a cross-sectional view of an encapsulation device. The cells are encapsulated in a lumen (114) by a two-layer membrane envelope, a vascularization membrane (120) and an immunoisolation membrane (130). The device (110) also has structural support, e.g., mesh, seals, etc.

In some embodiments, the encapsulation devices (110) comprise a vascularization membrane (120) and immunoisolation membrane (130). In some embodiments, the encapsulation devices (110) comprise just the vascularization membrane (120).

In the examples shown in FIG. 1A and FIG. 1B, the cells therein are about 5-15 μm in diameter. The outer membrane, the vascularization membrane (120), has a pore size from 5-10 μm. The vascularization membrane (120) is about 15 μm thick. The immunoisolation membrane (130) has a pore size of about 0.4 μm. The immunoisolation membrane (130) is about 30 μm thick. In some embodiments, the membranes (120, 130) are constructed from materials such as polytetraflouroethylene (PTFE) or other similar material. The present invention is not limited to the aforementioned pore sizes and thicknesses of the membranes used therein. The present invention is not limited to the aforementioned materials.

The encapsulation devices (110) may be constructed in various shapes and sizes and with various lumen volumes. For example, in some embodiments, the lumen has a volume of about 4.5 μl. In some embodiments, the lumen has a volume of 20 μl. In some embodiments, the lumen has a volume of 40 μl. In some embodiments, the device (110) is from 4 to 5 cm in length. In some embodiments, the device (110) is from 2 to 5 cm in length, e.g., 3 cm. In some embodiments, the device (110) is from 5 to 10 cm in length. The present invention is not limited to the aforementioned dimensions and lumen volumes. For example, in some embodiments, the lumen has a volume of about 100 μl. In some embodiments, the lumen has a volume of about 200 μl. In some embodiments, the lumen has a volume from 2 to 50 μl. In some embodiments, the lumen has a volume from 10 to 100 μl. In some embodiments, the lumen has a volume from 40 to 200 pl. In some embodiments, the lumen has a volume from 100 to 300 μl. In some embodiments, the lumen has a volume from 200 to 500 μl.

In some embodiments, within the encapsulation devices (110), there may be layers of cells or tissue, e.g., multiple lumens within the device (110). For example, an encapsulation device (110) may comprise two lumens or chambers. In some embodiments, the device comprises more than two lumens or chambers, e.g., 3 chambers or lumens, 4 chambers or lumens, 5 chambers or lumens, etc. FIG. 2A and FIG. 2B show examples an encapsulation with two lumens (two chambers) that are separated by a gas channel (160). FIG. 2A and FIG. 2B also show vascularizing membrane and microvasculature. The blood vessels embed into the vascularizing membrane.

In some embodiments, the chamber or lumen comprises a single layer of cells. In some embodiments, the chamber or lumen comprises two layers of cells. In some embodiments, the chamber comprises three or more layers of cells. In some embodiments, islet spheroids (about 150 um in size) are used (shown in FIG. 2A, FIG. 2B). In some embodiments, a dual layer of the islet spheroids is used (lumen thickness would be about 300 um in the chamber or in each chamber). In some embodiments, a third layer is supported depending on the metabolic activity and other characteristics of the spheroids/cells used. Note spheroids may not be touching each other in some configurations and the space between them may be 1 or 2 spheroids apart (e.g., 150 um, 300 um), or more or less.

Vascularization can occur around the encapsulation devices (110).

System with Encapsulation Device and Oxygen Sensors

The present invention features systems comprising encapsulation devices for cells and oxygen sensors. As shown in FIG. 3A, the system may comprise an encapsulation device (110) with loading ports (106, 107) and a lumen for holding cells. In some embodiments, one or more sensors (410) are disposed within the encapsulation device (110). In some embodiments, one or more sensors (410) are disposed on the outer surface of the encapsulation device (110). In some embodiments, one or more sensors are disposed on the loading ports (106, 107), e.g., the inlet and outlet. The sensors at the inlet and outlet may be integrated with a flow through cell (see FIG. 3B). The example shown in FIG. 3A comprises a bioreactor (105) with the encapsulation device (110) disposed therein (e.g., for storage prior to implantation). As an example, the sensors on the inlet and outlet of the system are for oxygen consumption rate measurements, which may be used as a means of evaluating viability of the device with cells.

FIG. 4 shows a system comprising an encapsulation device with two lumens of cells separated by a gas channel. A sensor (410) is disposed in the gas channel, and sensing particles (410a) are disposed on the outer surface of the device. Sensors may be at various different locations.

FIG. 5 shows a schematic view of an encapsulation device (single-chamber) comprising two sensors disposed in the lumen with the cells. As previously discussed, the sensors may be various types of sensors, e.g., oxygen sensor, glucose sensor, lactate sensor, combination thereof, etc. Sensors may be optical, electrochemical, NMR-based, or a combination thereof.

FIG. 6A shows a schematic view of a system with an optical reader (430) outside the body. The wireless reader (430) is external to the skin. The wireless reader can read the sensors (410) in the device (110) below the skin. FIG. 6B shows a schematic view of a system with optical readers (430) inside the body. The readers (430) can read the sensors (410) in the device, even through vasculature.

The sensors used in the systems of the present invention may be oxygen sensors, glucose sensors, pH sensors, lactate sensors, carbon dioxide sensors, the like, or a combination thereof. In some embodiments, the sensors are optical sensors, electrochemical sensors, NMR sensors, or a combination thereof.

In some embodiments, the system comprises two sensors and both sensors are oxygen sensors, e.g., the sensors are adapted to allow oxygen consumption rate (OCR) measurements. The sensors are placed such that they do not interfere with each other. In some embodiments, a first oxygen sensor is disposed at an inlet (e.g., oxygen channel) of the encapsulation device, and a second oxygen sensor is disposed at an outlet of the encapsulation device. The present invention is not limited to the sensors or placements described herein. In some embodiments, the system comprises two sensors. In some embodiments, the system comprises three sensors. In some embodiments, the system comprises four sensors. In some embodiments, the system comprises five sensors. In some embodiments, the system comprises six or more sensors.

The system of the present invention may further comprise a reader adapted to read one or all sensors. In some embodiments, the reader is an external reader. In some embodiments, the reader is an implantable reader (e.g., implantable optical reader).

In some embodiments, the system of the present invention further comprises an oxygen delivery system. As shown in FIG. 7A and FIG. 7B, oxygen may be delivered to the systems via several different mechanisms. For example, the system (100) of FIG. 7A is operatively and fluidly connected to an implantable oxygen generator (310). Tubing (350) delivers gas from the oxygen generator (310) to the device (110). Implantable oxygen generators are well known to one of ordinary skill in the art. For example, the implantable oxygen generator may feature an electrochemical oxygen generation mechanism (e.g., using electricity to break down water to oxygen hydrogen), a chemical mechanism, or other mechanism. In FIG. 7B, the system (100) is operatively and fluidly connected to a wearable oxygen generator (320) or pump via tubing. A special device (330) may be implanted into the skin to help prevent infection. In some embodiments, the oxygen is delivered via a carrier media like hemoglobin or fluorinated microbubbles. The present invention is not limited to the aforementioned systems or materials. In some embodiments, the oxygen generator provides oxygen for the lifetime of the implant (e.g., several years), or other length of time.

As previously discussed, in some embodiments, the systems of the present invention (e.g., encapsulation devices with oxygen sensors) are used with an oxygen delivery system. In some embodiments, the systems (e.g., encapsulation devices with oxygen sensors) of the present invention are used without an oxygen delivery system.

In some embodiments, the systems (e.g., encapsulation devices with oxygen sensors) of the present invention are temporarily oxygenated. For example, in some embodiments, oxygen is temporarily delivered initially (e.g., initially upon implantation) until the system is adequately vascularized. In some embodiments, oxygen may be temporarily delivered and/or oxygen levels may be variable. For example, in some embodiments, a cell type is used that benefits from a high oxygen level. In some embodiments, a cell type is used that benefits from a low oxygen level (e.g., 15% or lower). In some embodiments, an oxygen level of about 21% oxygen (e.g., 20-22%) is used, e.g., air may be used. In some embodiments, an oxygen level from 15-22% is used. In some embodiments, an oxygen level from 10-15% is used. In some embodiments, an oxygen level from 5-10% is used. In some embodiments, an oxygen level from 0-5% is used. In some embodiments, a particular oxygen level is used initially and then the oxygen level is increased or decreased at a later time. In some embodiments, oxygen is turned on and then off. In some embodiments, oxygen is turned off and then on. In some embodiments, oxygen is turned on and off in a cycle for a period of time or indefinitely. In some embodiments, oxygen level is tailored to the application to help modulate the local immune system by providing temporary oxygen. In some embodiments, oxygen levels are tailed to when vascularization occurs. In some embodiments, immature cells are transplanted, and low oxygen levels may be used initially; as the cells mature (e.g., after a particular time, e.g., 4-6 weeks), higher oxygen levels may be provided.

Without wishing to limit the present invention to any theory or mechanism, it is believed that the methods, systems, devices, and compositions of the present invention may help detect and regulate oxygen levels near or within encapsulation devices and alarm if not within the desired level. If insulin secreting cells are transplanted, the system may help regulate blood glucose by ensuring that the insulin secreting cells are properly oxygenated and therefore are able to release insulin in response to glucose in an appropriate manner.

In some embodiments, the system features a means of determining when the cells are dead (e.g., via oxygen sensors, monitoring oxygen consumption rate, etc.). Without wishing to limit the present invention to any theory or mechanism, cells are likely dead if there is generally no difference in oxygen levels inside and outside the device. Typically there is a difference (a gradient) in oxygen levels between the inside and outside of the device because oxygen is being consumed by live cells. Thus, no difference would be indicative of no oxygen consumption, thus the cells are likely dead. A bigger difference (gradient) in oxygen levels between the inside and outside of the device would indicate there are more viable cells. A user may determine how many cells are dying by determining the change in oxygen gradient.

In some embodiments, the sensors (e.g., oxygen sensors) are operatively connected to the exogenous oxygen delivery system via a sensor reader, e.g., a reader for reading the sensors. The reader may feature a microprocessor adapted to regulate the oxygen delivery of the exogenous oxygen delivery system. For example, if the microprocessor receives a first command from the reader that oxygen levels are low (e.g., below a threshold level), the microprocessor can send a command to the exogenous oxygen delivery system to increase oxygen delivery to the encapsulation device. In some embodiments, when the microprocessor receives a second command from the reader that oxygen levels are high (e.g., above a threshold level), the microprocessor can send a command to the exogenous oxygen delivery system to decrease oxygen delivery to the encapsulation device. In some embodiments, the system is operatively connected to an alarm system such that the patient is alerted when oxygen levels are low or high.

As previously discussed, the present invention also features an implantable sensor reader (e.g., implantable optical sensor reader) for reading sensors (e.g., optical sensors). In some embodiments, the implantable sensor reader is placed near or adjacent to the sensor. In some embodiments, the sensor reader can be implanted into the subject at any depth with respect to the skin. The implantable sensor reader is constructed from materials that are compatible for implantation. Note the sensor reader may not necessarily be physically connected (e.g., could be wireless).

The present invention also features methods for detecting vascularization of an encapsulation device of the present invention. The method may comprise monitoring oxygen levels (e.g., via a first oxygen sensor, a second oxygen sensor). An increase in oxygen levels without exogenous oxygen delivery may be indicative of vascularization of the encapsulation device (e.g., oxygen is delivered to the device via the blood vessels). In some embodiments, detection of vascularization may be an indication that exogenous oxygen delivery can be discontinued. The oxygen levels that would be indicative of sufficient vascularization may depend on the transplantation site. In some embodiments, it may be 1-20 mm Hg. In some embodiments, oxygen levels indicative of vascularization may be from 1-5 mm Hg. In some embodiments, oxygen levels indicative of vascularization may be from 5 to 10 mm Hg. In some embodiments, oxygen levels indicative of vascularization may be from 10 to 20 mm Hg. In some embodiments, oxygen levels indicative of vascularization may be from 15 to 25 mm Hg. In some embodiments, oxygen levels indicative of vascularization may be from 20 to 30 mm Hg. In some embodiments, oxygen levels indicative of vascularization may be from 30 to 40 mm Hg. In some embodiments, oxygen levels indicative of vascularization may be 40 mm Hg or more.

Without wishing to limit the present invention to any theory or mechanism, it is believed that the methods, systems, devices, and compositions of the present invention may help regulate blood glucose.

Implantation may be at any appropriate site, including but not limited to an arm location, a leg location, a torso location, etc.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An implantable encapsulation device for housing cells, the device comprising:
    a lumen for receiving and housing cells;
    a vascularization membrane at least partially surrounding the lumen, and wherein the vascularization membrane is permeable to cells and comprises pores of less than 10 micrometers;
    a gas delivery system operatively connected to the encapsulation device, wherein the gas delivery system comprises a gas channel operable to deliver gas to the device; and
    an oxygen delivery system comprising an implantable oxygen generator;
    a first sensor provided in the gas channel and a second sensor disposed on an outer surface of the encapsulation device; and
    wherein the sensors are operable to determine at least one of an oxygen level and an oxygen consumption rate.

2. The device of claim 1, wherein the sensors each comprise oxygen sensors that are collectively operable to determine an oxygen consumption rate of cells provided within the device.

3. The device of claim 1, further comprising an immunoisolation member provided adjacent the vascularization membrane.

4. The device of claim 1, wherein the device comprises a cell loading port that provides access to the lumen.

5. The device of claim 1, further comprising a reader adapted to read at least one of an oxygen level and an oxygen consumption rate.

6. The device of claim 5, wherein the reader comprises a wireless reader provided external to the lumen and operable to be provided external to the skin of a patient.

7. The device of claim 1, wherein at least one of the sensors is selected from the group comprising: oxygen sensors, glucose sensors, pH sensors, lactate sensors, carbon dioxide sensors, optical sensors, and electrochemical sensors.

8. An implantable encapsulation device for housing cells, the device comprising:
    a lumen for receiving and housing cells;
    a vascularization membrane at least partially surrounding the lumen, and wherein the vascularization membrane is permeable to cells;
    a first oxygen sensor provided proximal to an inlet of the lumen and wherein the first oxygen sensor is operable to determine an amount of oxygen at a first location in the device;
    a second oxygen sensor provided at a second location of the device and wherein the second oxygen sensor is operable to determine an amount of oxygen at the second location of the device; and
    wherein the first sensor and the second sensor are spaced apart by a physical distance to prevent interference between the sensors and wherein the sensors are operable to detect vascularization based on at least one of oxygen level and an oxygen consumption rate.

9. The device of claim 8, wherein the first oxygen sensor and the second oxygen sensor are positioned within an interior volume of the lumen.

10. The device of claim 8, further comprising an immuno-isolation member provided adjacent to the vascularization membrane.

11. The device of claim 8, wherein the device comprises a cell loading port that provides access to the lumen.

12. The device of claim 8, further comprising a reader adapted to read at least one of the first oxygen sensor and the second oxygen sensor.

13. The device of claim 12, wherein the reader comprises a wireless reader provided external to the lumen and operable to be provided external to the skin of a patient.

14. The device of claim 8, further comprising an oxygen delivery system comprising an implantable oxygen generator and a microprocessor that is operable to regulate oxygen delivery from the oxygen delivery system to the lumen.

15. A method for detecting vascularization of an implantable device, the method comprising:
providing an implantable device comprising a lumen for receiving and housing cells; a vascularization membrane at least partially surrounding the lumen, and wherein the vascularization membrane is permeable to cells; a first oxygen sensor and a second oxygen sensor, wherein the first oxygen sensor and the second oxygen sensor are positioned within an interior volume of the lumen and wherein the first oxygen sensor and the second oxygen sensor are spaced apart;
monitoring a first oxygen level at a first location of the implantable device by reading the first oxygen sensor;
monitoring a second oxygen level at a second location of the implantable device by reading the second oxygen sensor;
determining an oxygen consumption rate by comparing the first oxygen level and the second oxygen level and determining the viability of cells in the lumen based on the oxygen consumption rate; and
wherein vascularization is detected or determined based on at least one of the oxygen consumption rate and oxygen levels.

16. The method of claim 15, wherein a microprocessor and an oxygen delivery system are provided, and wherein the microprocessor commands the oxygen delivery system to increase oxygen delivery to the implantable device based on the oxygen consumption rate.

17. The method of claim 15, further comprising providing a wireless reader on a patient's skin.

* * * * *